US005736405A

United States Patent [19]
Alfano et al.

[11] Patent Number: 5,736,405
[45] Date of Patent: Apr. 7, 1998

[54] MONITORING BOILER INTERNAL TREATMENT WITH FLUORESCENT-TAGGED POLYMERS

[75] Inventors: Joseph C. Alfano, Lisle; Martin R. Godfrey, Elburn; Radhakrishnan Selvarajan, Downers Grove; Mary C. Uhing, Chicago, all of Ill.

[73] Assignee: Nalco Chemical Company, Naperville, Ill.

[21] Appl. No.: 621,152

[22] Filed: Mar. 21, 1996

[51] Int. Cl.⁶ .......................... G01N 33/18; G01N 33/44
[52] U.S. Cl. .......................... 436/55; 436/56; 436/119; 436/129; 436/172
[58] Field of Search .......................... 436/55, 56, 129, 436/119, 164, 172

[56] References Cited

U.S. PATENT DOCUMENTS

| | | |
|---|---|---|
| 4,048,066 | 9/1977 | Cuisia et al. . |
| 4,176,007 | 11/1979 | Frosch et al. . |
| 4,783,314 | 11/1988 | Hoots et al. . |
| 4,963,267 | 10/1990 | Hoots et al. . |
| 4,966,711 | 10/1990 | Hoots et al. . |
| 4,992,380 | 2/1991 | Moriarty et al. . |
| 5,006,311 | 4/1991 | Hoots et al. . |
| 5,035,806 | 7/1991 | Fong et al. . |
| 5,041,386 | 8/1991 | Pierce et al. . |
| 5,120,661 | 6/1992 | Baker et al. . |
| 5,124,047 | 6/1992 | Quach et al. . |
| 5,128,419 | 7/1992 | Fong et al. . |
| 5,132,096 | 7/1992 | Hoots et al. . |
| 5,166,074 | 11/1992 | Vessey et al. . |
| 5,171,450 | 12/1992 | Hoots . |
| 5,175,456 | 12/1992 | Neff et al. . |
| 5,178,771 | 1/1993 | Hayashibe et al. . |
| 5,183,574 | 2/1993 | Hwa et al. . |
| 5,200,106 | 4/1993 | Hoots et al. . |
| 5,216,086 | 6/1993 | Fong et al. . |
| 5,236,845 | 8/1993 | Pierce et al. . |
| 5,242,602 | 9/1993 | Richardson et al. .......... 436/171 X |
| 5,260,386 | 11/1993 | Fong et al. . |
| 5,266,493 | 11/1993 | Young . |
| 5,277,135 | 1/1994 | Dubin et al. . |
| 5,278,074 | 1/1994 | Rao . |
| 5,282,379 | 2/1994 | Harder et al. . |
| 5,389,548 | 2/1995 | Hoots et al. . |

FOREIGN PATENT DOCUMENTS

| | | |
|---|---|---|
| 2116737 | 3/1994 | Canada . |
| 2116816 | 3/1994 | Canada . |
| 5-277491 | 10/1993 | Japan . |

OTHER PUBLICATIONS

J. E. Hoots et al. *Mater. Perform.* 1992, 31, 46–51.
J. E. Hoots et al. *Ann. Univ. Ferrara, Sez. 5 Suppl.* 1995, 10, 533–542.
P. Ander et al. *Macromolecules* 1992, 15, 213–214.
N. J. Turro et al. *J. Phys. Chem.* 1982, 86, 1485–87.
J. M. Torkelson et al. *Polym. Prepr.* 1985, 26, 211–212.
C.-T. Chen et al. *Macromolecules* 1989, 22, 159–164.
I. Sekine et al. *J. Electrochem. Soc* 1992, 139, 3167–3173.
The Use of Sulfonated Styrene Copolymers as Boiler Water Sludge Conditioning Agents, P. E. Greenlimb,D. A. Cater—Dearborn Chemical no date available.
The Use of Sulfonated Styrence Copolymers for Boiler Scale Control, D. G. Cuisia, Dearborn Chemical no date available.
On–Line Monitoring of Boiler Water Polymer Dispersants, J. Richardson,R. Tippett, P. Gabris, Grace Dearborn 1993.
A Novel Polymer for Effective Boiler Water Scale Control, McDonough/Cuisia/Tippeta/Fan—NACE Corrosion 95, Paper No. 478 1995.

*Primary Examiner*—Arlen Soderquist
*Attorney, Agent, or Firm*—Robert A. Miller

[57] ABSTRACT

A method for the determination of the concentration of additives in boiler water systems, by which polymeric additives are utilized to monitor and treat boiler water systems.

18 Claims, 10 Drawing Sheets

MONITORING BOILER INTERNAL TREATMENT WITH FLUORESCENT-TAGGED POLYMERS

FIELD OF THE INVENTION

The invention is a method for the determining the concentration of additives in boiler water systems, more specifically, a method using polymers to monitor and treat the boiler water systems.

BACKGROUND OF THE INVENTION

Deposits, particularly scale, can form on boiler tubes. Each contaminant constituting the source of scale has an established solubility in water and will precipitate when that solubility has been exceeded. If the water is in contact with a hot surface and the solubility of the contaminant is lower at higher temperatures, the precipitate will form on the surface, causing scale. In addition, the formation of steam bubbles at a surface causes increases in the concentration of soluble components at the steam/water interface that can cause precipitation. The most common components of boiler deposits are calcium phosphate, calcium carbonate (in low-pressure boilers), magnesium hydroxide, calcium and magnesium silicates, various forms of iron oxide, and silica.

At the high temperatures found in a boiler, deposits are a serious problem causing poor heat transfer and a potential for boiler tube failure. In low-pressure boilers with low heat transfer rates, deposits may build up to a point where they completely occlude the boiler tube.

In modern intermediate and higher pressure boilers with heat transfer rates in excess of 200,000 Btu/ft²hr (5000 cal/m²hr), the presence of even extremely thin deposits will cause a serious elevation in the temperature of tube metal. The deposit retards transfer of heat from the furnace gases into the boiler water. This heat resistance results in a rapid rise in metal temperature to the point at which failure can occur.

Deposits may be scale, precipitated in situ on a heated surface, or previously precipitated chemicals, often in the form of sludge. These collect in low-velocity areas, compacting to form a dense agglomerate similar to scale. In the operation of most industrial boilers, it is seldom possible to avoid formation of some type of precipitate at some time. There are almost always some particulates in the circulating boiler water which can deposit in low-velocity sections.

Boiler feedwater, charged to the boiler, regardless of the type of treatment used to process this source of makeup, still contains measurable concentrations of impurities. In some plants, contaminated condensate contributes to feed water impurities.

When steam is generated from the boiler water, water vapor is discharged from the boiler, with the possibility that impurities introduced in the feed water will remain in the boiler circuits. The net result of impurities being continuously added and pure water vapor being withdrawn is a steady increase in the level of dissolved solids in the boiler water. There is a limit to the concentration of each component of the boiler water. To prevent exceeding these concentration limits, boiler water is withdrawn as blowdown and discharged to waste. Blowdown must be adjusted so that the concentration of impurities in the boiler water are maintained at predetermined limits. Scale inhibition has been accomplished by chelating agents which control the activity of metal ions by blocking the reactive sites of the metal ions thus preventing reactions between the metal cations and anions in the system. In addition, polymer programs work much like the chelating agents in controlling scaling in boiler water systems.

Substantial heat energy in the blowdown represents a major factor detracting from the thermal efficiency of the boiler, so minimizing blowdown is a goal in every steam plant.

One way of looking at boiler blowdown is to consider it a process of diluting boiler water impurities by withdrawing boiler water from the system at a rate that induces a flow of feed water into the boiler in excess of steam demand.

Blowdown used for adjusting the concentration of dissolved solids (impurities) in the boiler water may be either intermittent or continuous. If intermittent, the boiler is allowed to concentrate to a level acceptable for the particular boiler design and pressure. When this concentration level is reached, the blowdown valve is opened for a short period of time to reduce the concentration of impurities, and the boiler water impurities are then allowed to re-concentrate until the control limits are again reached. In continuous blowdown, on the other hand, which is characteristic of all high pressure boiler systems, virtually the norm in the industry, the blowdown valve is kept open at a fixed setting to remove water at a steady rate, maintaining relatively constant boiler water concentration.

U.S. Pat. No. 5,260,386 issued to Fong et al. on Nov. 9, 1993 discloses a method of preparing, by a (trans) amidation reaction, a polymer having pendant fluorescent groups having amine-containing organic fluorescent groups having the formula:

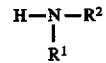

This is a method of tagging pre-existing polymers without any deleterious effects on the polymer.

U.S. Pat. No. 5,389,548 issued to Hoots et al. on Feb. 14, 1995 teaches a method of monitoring and controlling the concentration of polyelectrolytes. A sample is drawn and a known amount of a fluorochromatic reagent is added. Analysis is completed by measuring the amount of the dye available for light absorption. A comparison of the fluorescence emission of the reagent to the fluorescence emission of the polyelectrolyte and to the concentration of the polyelectrolyte, thereby allows the determination of the polyelectrolyte concentration.

U.S. Pat. No. 5,128,419 issued to Fong et al. on Jul. 7, 1992 and U.S. Pat. No. 5,216,086 issued to Fong et al. on Jun. 1, 1993, incorporated hereinto by reference, describe a post-polymerization derivation method for preparing polymers having pendant fluorescent groups. Polymers so marked or tagged may be monitored by fluorescence spectroscopy to determine the location, route, concentration at a given site and/or some property (for instance leachability) of these polymers and/or a substance in association with these polymers. As discussed herein, conventional techniques from monitoring polymers are generally time consuming and labor intensive, and often require the use of cumbersome and/or costly equipment.

Most conventional polymer analysis techniques require the preparation of calibration curves for each type of polymer employed, which is particularly time consuming and laborious when a large variety of polymer chemistries are being employed. Conventional analysis techniques that determine analytically the concentration of a polymer's functional group are generally not practical for industrial use, particularly when it is desired to monitor a polymer on a frequent or continuous basis, or when rapid results are needed. Indirect analysis techniques may provide results faster using simpler techniques, but in many instances even faster and/or more accurate determinations are highly desirable.

If the fluorescent group incorporated into a polymer is derived from a highly fluorescent molecule, its presence will permit the monitoring of the polymer at concentration levels down to 0.1 ppm or less, even when the polymer is tagged with only one part by weight of the fluorescent group per 100 parts by weight of polymer. The post polymerization is a (trans) amidation derivation of preexisting polymers having carbonyl-type pendant groups, including pendant carboxylic acid, carboxylic acid ester and amide groups.

This post-polymerization derivation method is exemplified in U.S. Pat. No. 5,128,419 using a variety of starting-material polymers, including acrylic acid homopolymers, acrylic acid/acrylamide co-polymers, acrylic acid/acrylamide ter-polymers with sulfomethylacrylaimide, vinyl acetate, acrylonitrile and methacrylic acid.

U.S. Pat. No. 4,783,314 issued to Hoots et al. on Nov. 8, 1988, incorporated hereinto by reference, provides a method for monitoring a water treatment component by incorporating at least one fluorescent compound as a tracer into the treatment formulation to provide quantitative measurement/control of the treatment feed rate and performance. The concentration of a given fluorescent tracer in the aqueous system at a given point in time is generally determined by comparing the fluorescence emission of a sample from the system to a standard or a standard curve of fluorescent tracer concentration verses emissivity. Suitable fluorescence tracers for this method are substantially both water soluble and inert in the environment of the aqueous system in which they are used.

U.S. Pat. No. 4,801,388 issued to Fong et al. on Jan. 31, 1989, incorporated hereinto by reference, describes water-soluble polyelectrolytes which are effective as scale inhibitors and dispersants, and methods for preparing such polyelectrolytes by post-polymerization derivation. Such polyelectrolytes are examples of the wide range of mer unit types that may be included in a polymeric scale inhibitor. The amount of such polyelectrolytes used in an aqueous system is described as preferably in the range of from about 1 to about 200 ppm. The co-polymers and ter-polymers are described as having hydrocarbon roots containing an amino functionality.

U.S. Pat. No. 4,048,066 issued to Cuisia et al. on Sep. 13, 1977 discloses a method for inhibiting scale on heating surfaces of aqueous systems. Compositions discussed include co-polymers of styrene sulfonic acid with acrylic or methacrylic acid, and water-soluble salts there of or mixtures of polystyrene sulfonic acid with polyacrylic or polymethacrylic acid and water-soluble salts thereof.

U.S. Pat. No. 4,166,105 issued to Hirschfeld on Aug., 28, 1979 discloses a detection reagent reactive with an analyte body that is a polymer coupled to an antibody. The polymer has a plurality of fluorescent dye molecules coupled to it, covalently bonded through an aldehyde linkage at side reactive sites. The reagent can be a protein, antibody such as hepatitis B antigen. The reagent is used for antibody immunofluorescence.

U.S. Pat. No. 5,411,889 issued to Hoots et al. on May 2, 1995, incorporated hereinto by reference, provides a target-specie responsive regulation of a water treatment agent feed is achieved by monitoring of a subject target-specie indicator or a combination of an incipient and a target specie. The concentration adjustments are not contingent on water treatment agent residual level determinations, such as using calcium or iron concentrations in a system where the treatment agent is an anti-scalant.

U.S. Pat. No. 5,183,574 issued to Hwa et al. on Feb. 2, 1993 discloses a method of dispersing iron in an aqueous system using a co-polymer of styrene sulfonic acid and methacrylic acid or its water-soluble salt thereof. The mole ratio of sodium styrene sulfonate to methacrylic acid is in the range of 5:95 to 95:5, 10:90 to 90:10, and 20:80 to 80:20.

U.S. Pat. No. 5,124,047 issued to Quach et al. on Jun. 23, 1992 teaches a method of inhibiting scale formation in aqueous systems using allylphosphonate co-polymers which exhibit characteristic properties of a treating agent, namely, strong calcium complexion, iron dispersion, inhibition of calcium carbonate scale and inhibition of calcium phosphate deposition.

U.S. Pat. No. 5,006,311 issued to Hoots et al. on Apr. 9, 1991, incorporated hereinto by reference, provides a method of analyzing the level of a treating agent, using inert transition metal tracer added in proportion to the treating agent by determining the absorbance of a reagent dye added to a sample of the system. A second absorbance value is measured when the dye is reacted at the same concentration with the tracer. A third absorbance value is measured when the dye is reacted at the same concentration with the transitional metal contained in the system. Resolving the difference between the second and third absorbance values allows determination of the concentration of the tracer.

U.S. Pat. No. 5,171,450 issued to Hoots et al. on Dec. 15, 1992, incorporated hereinto by reference, discloses a method monitoring and controlling dosage of a treating agent to inhibit scale or corrosion. The treating agent contains an amine-containing fluorescent moiety tag covalently bonded to the pre-existing treating agent.

Canadian Patent Application No. 2,116,737, filed on Mar. 1, 1994, covers a method for monitoring the concentration of tagged polymers in boilers by obtaining the absorption or emission spectrum of the system water and submitting this spectrum to chemometric analysis. However, the application doesn't provide a clear method to determine if the polymer is degrading. The application assumes that when polymer degradation occurs, polymer degrades into a compound with little or no light absorbance or emission properties. In addition, changes in a "polymer concentration reading" can occur from a number of sources (besides polymer degradation considered in the application), including contaminants, cell fouling changes in light source, and changes in transmission properties of fiber optics.

Canadian Patent Application No. 2,116,816, filed on Mar. 2, 1994, discloses use of any water soluble polymer that contains a spectroscopically-accessible moiety and a high Ca cloud point (good calcium ion tolerance). Chemistry systems used include AA/SS for hardness transport in boilers. The application also discusses monitoring any water soluble polymer having a spectroscopically-accessible moiety and a high Ca cloud point by obtaining the in situ absorption spectrum followed by chemometric analysis.

U.S. Pat. No. 5,435,969 issued to Hoots et al. on Jul. 25, 1995, incorporated hereinto by reference, discloses a method for a concentration-fluctuation responsive regulation of a treating agent feed. An incipient is added to the sample drawn from the water system, whereby a concentration indicator is formed. The indicator is monitored by fluorescence analysis, determining at least one fluorescence emission value corresponding to the treating agent concentration in the system.

In many fields that employ polymers, it may be desirable to use polymers containing pendant fluorescent groups thereby facilitating the monitoring of such polymers. By the term "monitoring" is meant herein any type of tracking to determine the location or route of the polymers, and any type of determination of the concentration of the polymer at any given site, including singular or intermittent or continuous monitoring. For instance, it may be desirable to monitor water treatment polymers in water systems, particularly industrial water systems, or to monitor polymers that may be present in waste fluids before disposal, particularly industrial waste fluids, or to monitor the polymer used for down-hole oil well applications, particularly the route taken after introduction down-hole, or to monitor polymers that may be present in fluids used to wash a manufactured product, for instance a polymer-coated product, to determine the amount of polymer washed or leached therefrom. By fluids or liquids as used herein generally is meant aqueous, non-aqueous, and mixed aqueous/non-aqueous fluid systems. As seen from the above list of possible applications of polymer monitoring, the purpose of such monitoring may be to trace or track or determine the level of the polymer itself, or to trace or track or determine the level of some substance in association with the polymer, or to determine some property of the polymer or substance in association with the polymer, for instance its leachability or consumption, including a hydrothermal reaction, within the system.

Conventional techniques for monitoring polymers are generally time-consuming and labor intensive, and often require the use of bulky and/or costly equipment. Most conventional polymer analysis techniques require the preparation of chemical reagents and calibration curves for each type of polymer employed, which is time-consuming and laborious, particularly when a large variety of polymer chemistries is being employed, and the originally prepared calibration curves lose their accuracy if the polymer structures change, for instance an acrylic acid ester mer unit being hydrolyzed to an acrylic acid mer unit. Direct methods wherein the level of functional groups present in a polymer is determined analytically are generally not practical for industrial use, particularly when it is desired to monitor a polymer on a frequent or continuous basis, or when rapid monitoring results are needed. Indirect methods of polymer monitoring may provide results using simpler techniques, but in many instances faster and/or more accurate determinations are desirable.

Polymers containing pendant fluorescent groups are generally easily monitored, even when present at low concentrations. Highly fluorescent molecules, that is molecules which have a fluorescent quantum efficiency, or fluorescent quantum yield, within the range of from about 0.02 to about 1.0, and a light absorbance molar extinction coefficient of at least 300, are typically detectable at concentration ranges of parts per million ("ppm") to parts per billion ("ppb") or even less. The incorporation of such a highly fluorescent species, in this case sodium styrene sulfonate, into a polymer in the amount of from about one mole percent (based on polymer actives) to about 30 mole percent will permit the detection of such polymer at polymer concentration levels down to 0.1 ppm or less. More preferably, an effective incorporation of the sodium styrene sulfonate monomer is in the range from about 5 mole percent to about 15 mole percent. The most preferable incorporation range for the sodium styrene sulfonate monomer is from about 8 mole percent to about 12 mole percent wherein 10 mole percent is preferred.

It would be desirable to provide a method of using polymers containing pendant fluorescent groups. It would be desirable to provide a method wherein such a polymer would permit instantaneous and continuous monitoring of the water confined within the system, such as monitoring the feed water polymer concentration without the addition of chemical reagents or inert tracers. It would be desirable to provide a method that minimizes the reaction steps required and minimizes the time required for such monitoring as well as a method that does not require an operator to obtain a system water absorption or emission spectra, or employ chemometric analysis.

It would be desirable to provide a method in which the concentration of the polymer is compared to the concentration of an inert tracer to detect specific consumption of the polymer within the system, such as precipitation and hydrothermal reaction. It would be desirable to provide such a method that can be utilized in determining cycles of concentration within a particular system, for example, the measurement of boiler cycles.

It would be desirable to provide such a method wherein the system consumption, such as a hydrothermal reaction, of the polymer can be monitored spectroscopically. It would be desirable to provide such a method wherein a typical treatment dosage concentration of polymer may be utilized.

It would also be desirable to provide a method wherein the polymer enables accurate determination of the optimum product dosage needed for treatment within a system. These and other objects are provided by the present invention which is described in more detail below.

SUMMARY OF THE INVENTION

One embodiment of the invention is the method for determining a concentration of an anionically charged water soluble boiler water treatment polymer in a boiler water system. The boiler water system includes a source of a feedwater stream to the system as a first system parameter, a source of a blowdown stream from the system as a second system parameter, as well as a source of the soluble polymer in the boiler water as a third system parameter. The soluble polymer may undergo a hydrothermal reaction at boiler water system operating conditions. The soluble polymer contains at least 0.01% mer units of spectrophotometrically emitting moieties bound to the polymer chain. The method comprises the steps of:

a. measuring at least one spectrophotometric characteristic of the soluble polymer contained in a sample of the boiler water;

b. converting the characteristic to an electrical signal corresponding to the concentration of the soluble polymer in the boiler water;

c. comparing the electrical signal corresponding to the concentration of the soluble polymer in the boiler water to an electrical signal corresponding to a desired concentration of the soluble polymer in the boiler water; and then, d. determining a gain or loss of the soluble polymer in the boiler water.

DESCRIPTION OF THE PREFERRED EMBODIMENTS

Figure 1:
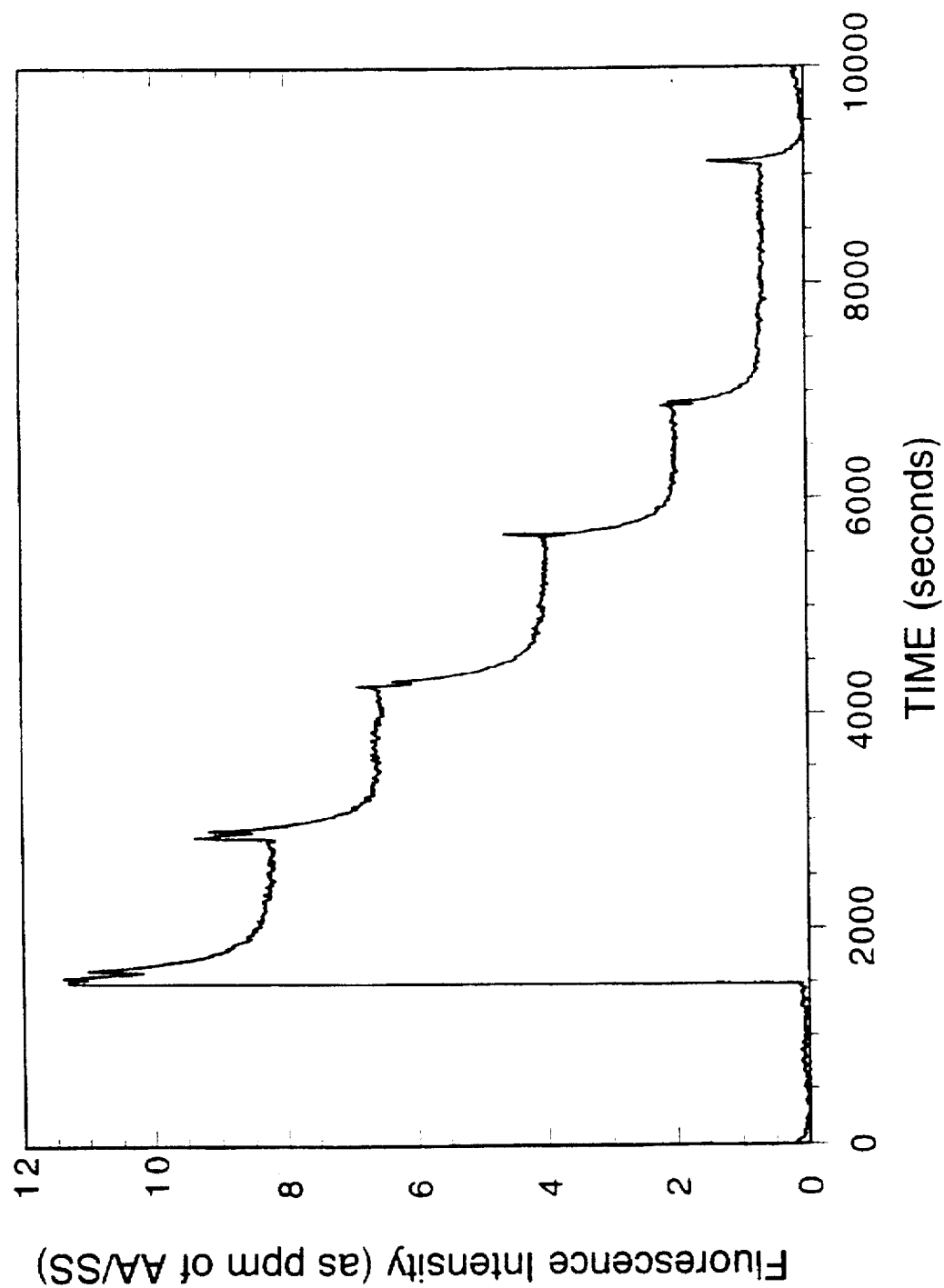
FIG. 1 is a line graph showing fluorescence intensity over time.

One embodiment of the invention is the method for determining a concentration of an anionically charged water soluble boiler water treatment polymer in a boiler water system. The boiler water system includes a source of a feedwater stream to the system as a first system parameter, a source of a blowdown stream from the system as a second system parameter, as well as a source of the soluble polymer in the boiler water as a third system parameter. The soluble polymer may undergoe a hydrothermal reaction at boiler water system operating conditions. The soluble polymer contains at least 0.01% mer units of spectrophotometrically emitting moieties bound to the polymer chain. The method comprises the steps of:

a. measuring at least one spectrophotometric characteristic of the soluble polymer contained in a sample of the boiler water;
   b. converting the characteristic to an electrical signal corresponding to the concentration of the soluble polymer in the boiler water;
   c. comparing the electrical signal corresponding to the concentration of the soluble polymer in the boiler water to an electrical signal corresponding to a desired concentration of the soluble polymer in the boiler water; and then,
   d. determining a gain or loss of the soluble polymer in the boiler water.

According to another embodiment of the invention, a sample of the boiler water containing the soluble polymer may be continuously passed through a flow cell. As such, a spectrophotometric characteristic of the polymer may be continuously measured, thereby continuously determining the gain or loss of soluble polymer in the system. Because the concentration (and ultimately, control of) treatment agents can be done monitoring the feedwater or the blowdown water, the use of the term boiler water will include either analysis unless the analysis is otherwise specified.

In addition, when the comparison of step d indicates the gain or loss of the soluble polymer, at least one of system parameters, namely, a feedwater stream flow rate into the boiler water system, a blowdown stream feed rate from the boiler water system, and a rate at which the soluble polymer is added to the feedwater stream of the boiler water system, may be altered, whereby the desired concentration of the soluble polymer is maintained in the boiler water.

At least one of the spectrophotometrically emitting moieties may be a styrene sulfonate group. While the preferred form of the styrene sulfonate group is the para-styrene sulfonate group, other forms, including meta and ortho styrene sulfonate groups may be used. The soluble polymer may contain carboxylate-containing mer units selected from the group consisting of acrylic acid, methacrylic acid, crotonic acid, vinyl acetic acid, 4-methyl-4 pentenoic acid, maleic acid, and itaconic acid, as well as others. Additionally, the soluble polymer may contain non-carboxylate containing mer units selected from the group consisting of sodium vinylsulfonate, vinylphosphonic acid, isopropenylphosphate, allyl polyethers, 2-acrylamido-2-methylpropane sulfonic acid, allylsulfonic acid, allyl alcohol, hydroxyethyl methacrylate, N-vinylimidazole, 2-vinylpyrolidine, 4-vinylpyridine, and vinylacetate, as well as others. The soluble polymer may contain at least 10% mer units of acrylic acid or water soluble salts of acrylic acid.

In another embodiment of the invention, the spectrophotometric characteristic sensed may be a fluorescent characteristic. The electrical signal corresponding to the concentration of the soluble polymer may be continuously compared to the electrical signal corresponding to the desired concentration of the soluble polymer. In addition, the electrical signal corresponding to the concentration of the soluble polymer may be intermittently compared to the electrical signal corresponding to the desired concentration of the soluble polymer.

Another embodiment of the invention is the method for determining a gain or loss as well as the addition amount of an anionically charged water soluble boiler water treatment polymer in a boiler water system. The boiler water system includes a source of a feedwater stream to the system as a first system parameter, a source of a blowdown stream from the system as a second system parameter, as well as a source of the soluble polymer in the boiler water as a third system parameter The soluble polymer may undergoe a hydrothermal reaction at boiler water system operating conditions. The soluble polymer contains at least 0.01% mer units of spectrophotometrically emitting moieties bound to the polymer chain. The method comprises the steps of:

a. adding a substantially inert tracer that is substantially inert to the system in a known ratio to the soluble polymer;
   b. measuring at least one spectrophotometric characteristic of the soluble polymer and measuring at least one spectrophotometric characteristic of the tracer contained in a sample of the boiler water;
   c. converting each of the characteristics to electrical signals corresponding to the concentration of the soluble polymer and concentration of the tracer, respectively; and,
   d. comparing the electrical signal corresponding to the soluble polymer concentration to the electrical signal corresponding to the tracer concentration, thereby determining the gain or loss of the soluble polymer in the system and the amount of soluble polymer added to the system.

A sample of the boiler water containing the soluble polymer may be continuously passed through a flow cell. As such, a spectrophotometric characteristic of the polymer may be continuously measured, thereby continuously determining the gain or loss of soluble polymer in the system.

In addition, an alarm may be activated when the comparison of step d indicates a gain or loss of the soluble polymer. When such a gain or loss of soluble polymer is indicated, at least one of the system parameters, namely, a feedwater stream flow rate into the boiler water system, a blowdown stream flow rate from the boiler water system, and a rate at which the soluble polymer is added to the boiler water system, may be altered, whereby a desired concentration of the soluble polymer may be maintained in the boiler water system.

At least one of the spectrophotometrically emitting moieties of the soluble polymer may be a styrene sulfonate group. The soluble polymer may contain carboxylate-containing mer units selected from the group consisting of acrylic acid, methacrylic acid, crotonic acid, vinyl acetic acid, 4-methyl-4 pentenoic acid, maleic acid, and itaconic acid. Additionally, the soluble polymer may contain non-carboxylate containing mer units selected from the group consisting of sodium vinylsulfonate, vinylphosphonic acid, isopropenylphosphate, allyl polyethers, 2-acrylamido-2-methylpropane sulfonic acid, allylsulfonic acid, allyl alcohol, hydroxyethyl methacrylate, N-vinylimidazole, 2-vinylpyrolidine, 4-vinylpyridine, and vinylacetate. The soluble polymer may contain at least 10% mer units of acrylic acid or water soluble salts of acrylic acid.

The electrical signal corresponding to the concentration of the soluble polymer may be continuously compared to the electrical signal corresponding to the tracer concentration. The electrical signal corresponding to the concentration of the soluble polymer may be intermittently compared to the electrical signal corresponding to the tracer concentration. The spectrophotometric characteristics sensed may be fluorescent characteristics.

Another embodiment of the invention is a method of determining boiler cycles of concentration in a boiler water system containing an anionically charged water soluble boiler water treatment polymer. The boiler water system includes a source of a feedwater stream to the system as a first system parameter, a source of a blowdown stream from the system as a second system parameter, as well as a source of the soluble polymer in the boiler water as a third system parameter. The soluble polymer undergoes a hydrothermal reaction at boiler water system operating conditions. The soluble polymer contains at least 0.01% mer units of spectrophotometrically emitting moieties bound to the polymer chain. The method comprises the steps of:

a. adding the soluble polymer to a feedwater stream entering the boiler water system;

b. measuring at least one spectrophotometric characteristic of the soluble polymer contained in a sample of the feedwater stream;

c. allowing at least a portion of the soluble polymer to hydrothermally react into a reaction product as the soluble polymer passes through the boiler water system;

d. measuring at least one spectrophotometric characteristic of the remaining soluble polymer and measuring at least one spectrophotometric characteristic of the reaction product contained in a sample of the blowdown stream;

e. converting each of the measured characteristics to electrical signals corresponding the concentration of the soluble polymer in the feedwater stream, the concentration of the remaining soluble polymer in the blowdown stream, and the concentration of the reaction product in the blowdown stream, respectively; and, f. using the concentration of the soluble polymer in the feedwater stream, the concentration of the remaining soluble polymer in the blowdown stream and the concentration of the reaction product in the blowdown stream to determine the boiler cycles of concentration of the boiler system.

The sample of the feed water stream containing the soluble polymer may be continuously passed through a flow cell. As such, at least one spectrophotometric characteristic of the soluble polymer may be continuously measured, thereby continuously determining the boiler cycles of concentration in the system.

A sample of the blowdown stream containing the remaining soluble polymer and reaction product may be continuously passed through a flow cell. As such, at least one spectrophotometric characteristic of the remaining soluble polymer and at least one spectrophotometric characteristic of the reaction product may be continuously measured, thereby the boiler cycles of concentration in the system is continuously determined.

Another embodiment of the invention is a method for spectrophotometrically monitoring a soluble polymer recovery value in a boiler water system containing an anionically charged water soluble boiler water treatment polymer. The boiler water system includes a source of a feedwater stream to the system as a first system parameter, a source of a blowdown stream from the system as a second system parameter, as well as a source of the soluble polymer as a third system parameter. The soluble polymer passes through the boiler water system under boiler water system operating conditions. The soluble polymer contains at least 0.01% mer units of spectrophotometrically emitting moieties bound to the polymer chain. The method comprises the steps of:

a. adding the soluble polymer to a feedwater stream of the boiler system;

b. allowing at least a portion of the soluble polymer to hydrothermally react into a reaction product as the soluble polymer passes through the boiler water system;

c. measuring at least one spectrophotometric characteristic of the remaining soluble polymer and at least one spectrophotometric characteristic of the reaction product in a sample of the blowdown stream;

d. converting each of the measured characteristics to electrical signals corresponding to the concentration of the remaining soluble polymer in the blowdown stream and the concentration of the reaction product in the blowdown stream, respectively; and, e. using the concentrations of the remaining soluble polymer in blowdown stream and the concentration of the reaction product in the blowdown stream to determine the soluble polymer recovery value within the boiler water system.

A sample of the blowdown stream containing the remaining soluble polymer and the reaction product may be continuously passed through a flow cell. As such, at least one spectrophotometric characteristic of the remaining soluble polymer and at least one spectrophotometric characteristic of the reaction product may be continuously measured, thereby the soluble polymer recovery value within the boiler water system is continuously determined.

The soluble polymer recovery value for the boiler water system may be used to determine an optimum concentration of the soluble polymer needed to effectively treat the boiler water system.

1) Feedwater Control

Figure 2:
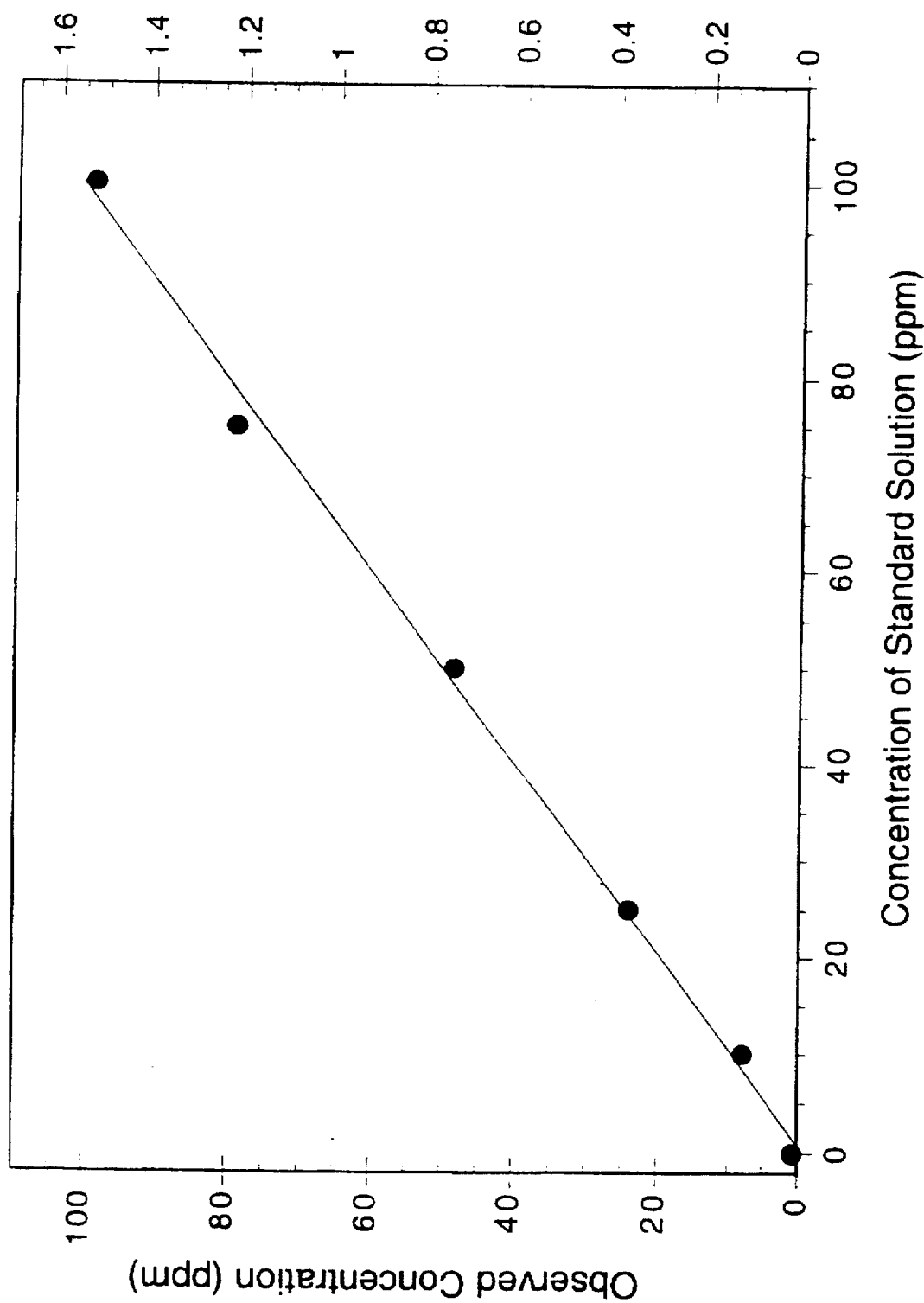
FIG. 2 is a line graph showing the comparison of the known concentration of a standard and the observed concentration of the standard using the invention.

The polymer of the invention would allow for instantaneous and continuous monitoring of the feedwater polymer concentration without the addition of chemical reagents or an inert tracer. This is accomplished by monitoring the fluorescence intensity of the treating agent at at least a single set of excitation and emission wavelengths. As mass flow rates in the boiler system change, the concentration of polymer in the feedwater may also change. This change in concentration would be reflected as a change in fluorescence intensity as measured at the set of excitation and emission wavelengths. This capability permits automated boiler chemical feed, with the feed rate of the internal treatment chemical (treating agent) automatically varying to adjust for swings in boiler feed water mass flow rates (which can be caused by varying steaming rates, blowdown flow rates and other variables). Monitoring of the polymer could also be used to control the feed rate of other chemicals that would be delivered to the system in fixed proportion to the polymer. FIG. 1 shows an example of an on-line measurement of styrene sulfonate, "SS", fluorescence at various polymer concentrations. (Excitation wavelength was 254 nm and emission wavelength was 300 nm.) FIG. 1 shows the detection limit measurement. FIG. 2 shows an example of the correlation between the actual polymer concentration (measured using laborious laboratory based procedures) and the concentration as measured by SS fluorescence (for AA/SS as 95/5 mole %).

2) Polymer Precipitation and Hydrothermal Reactions

The polymer concentration can be compared to that of the concentration of an inert tracer to detect specific gain or loss of the polymer (treating agent) due to precipitation, re-dissolution, or hydrothermal reaction. This is accomplished by monitoring the fluorescence intensity of the treatment agent (polymer) at a single set of excitation and emission wavelengths and monitoring the fluorescence intensity of the inert tracer at a different set of excitation and emission wavelengths. (As the polymer undergoes a gain or loss, such change is reflected in a change of intensity at the set of wavelengths, which can be measured spectrophotometrically.) For example, if a hardness upset occurred, it may cause precipitation of the polymer, which could be monitored by following the decrease in the acrylic acid/styrene sulfonate polymer, "AA/SS", fluorescence compared to the fluorescence of the inert tracer in the boiler blowdown.

Figure 3:
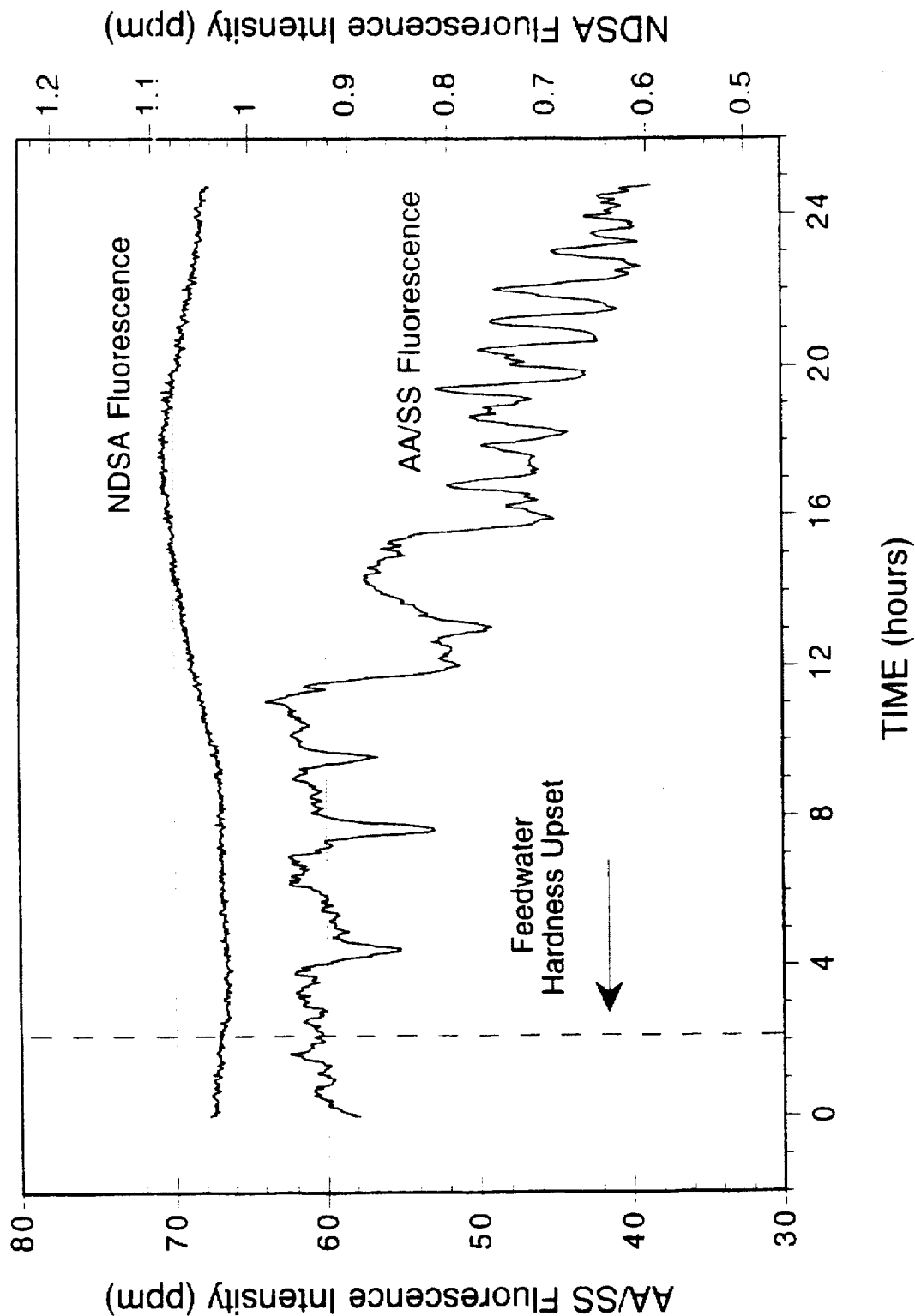
FIG. 3 is a graph showing the real time detection of polymer precipitation.

An example of this is given in FIG. 3, showing treating a simulated hardness upset with AA/SS at 99/1 mole %. In a boiler system, harsh feedwater hardness upset conditions were created by adding 5.5 ppm Ca (as $CaCO_3$) to the feedwater. The blowdown inert tracer, 1.0 ppm of 1,5-naphthalene disulfonic acid (NDSA), concentration represented by the dashed line, was unaffected by the upset, since it is inert. The AA/SS polymer containing 1 mole percent of SS, however, precipitated as a calcium salt, as indicated by the drop in AA/SS polymer fluorescence after the upset. The AA/SS polymer fluorescence is represented by the solid line.

The AA/SS polymer fluorescence can also be used to measure boiler cycles. Before this application can be described, it is necessary to give some background information. Under conditions typical to many boilers, the AA/SS polymer undergoes partial hydrothermal reaction, and this reaction can be followed spectroscopically. As the polymer undergoes the hydrothermal reaction, the change in concentration is reflected in a change in the spectrophotometric intensity at the wavelengths of the polymer. This was demonstrated by heating a solution of AA/SS polymer at 600 psig (254° C.) and pH=11 and measuring its fluorescence properties as a function of time.

Figure 4:
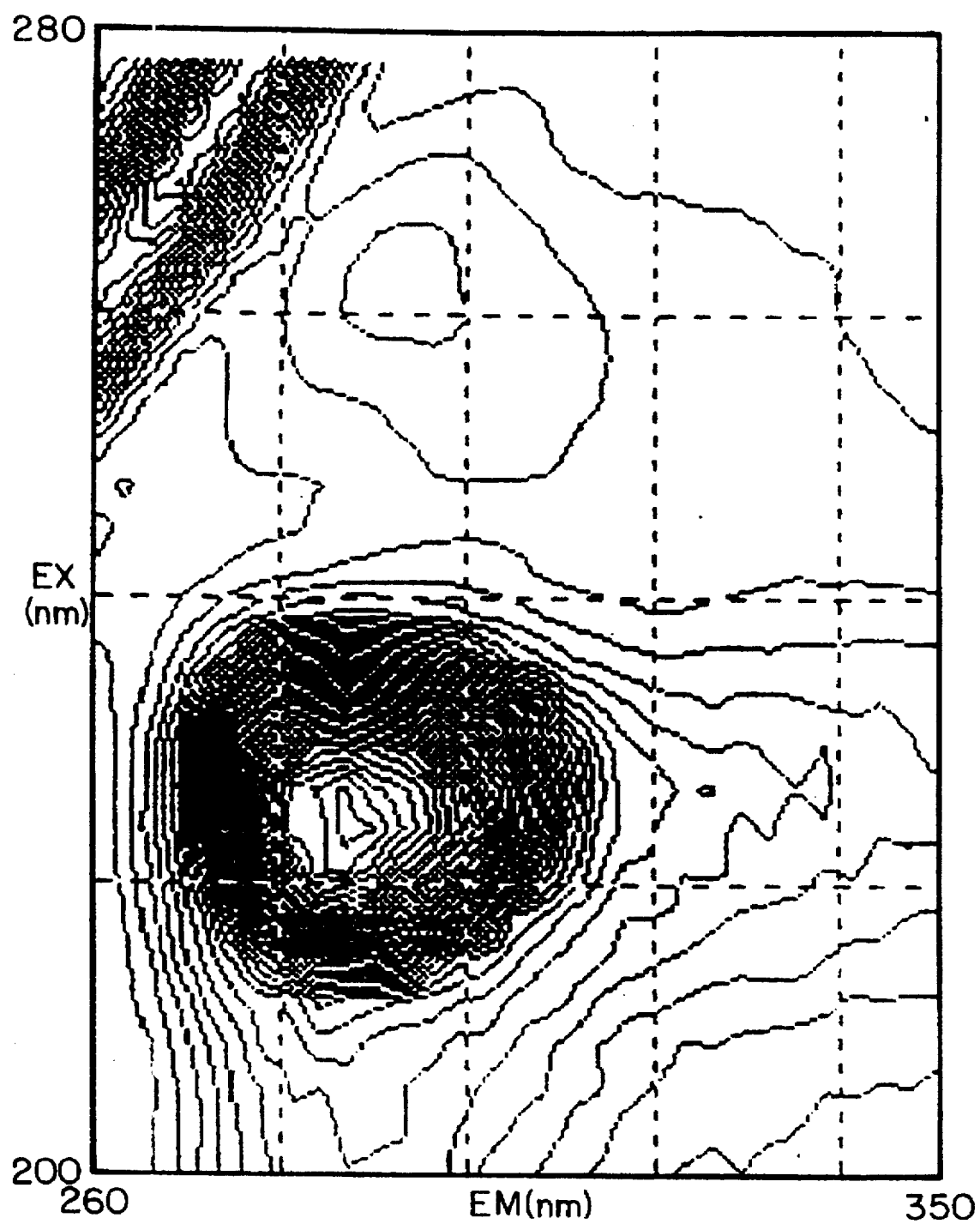
FIG. 4 is a fluorescence contour plot showing the kinetics of the hydrothermal reaction.
Figure 5:
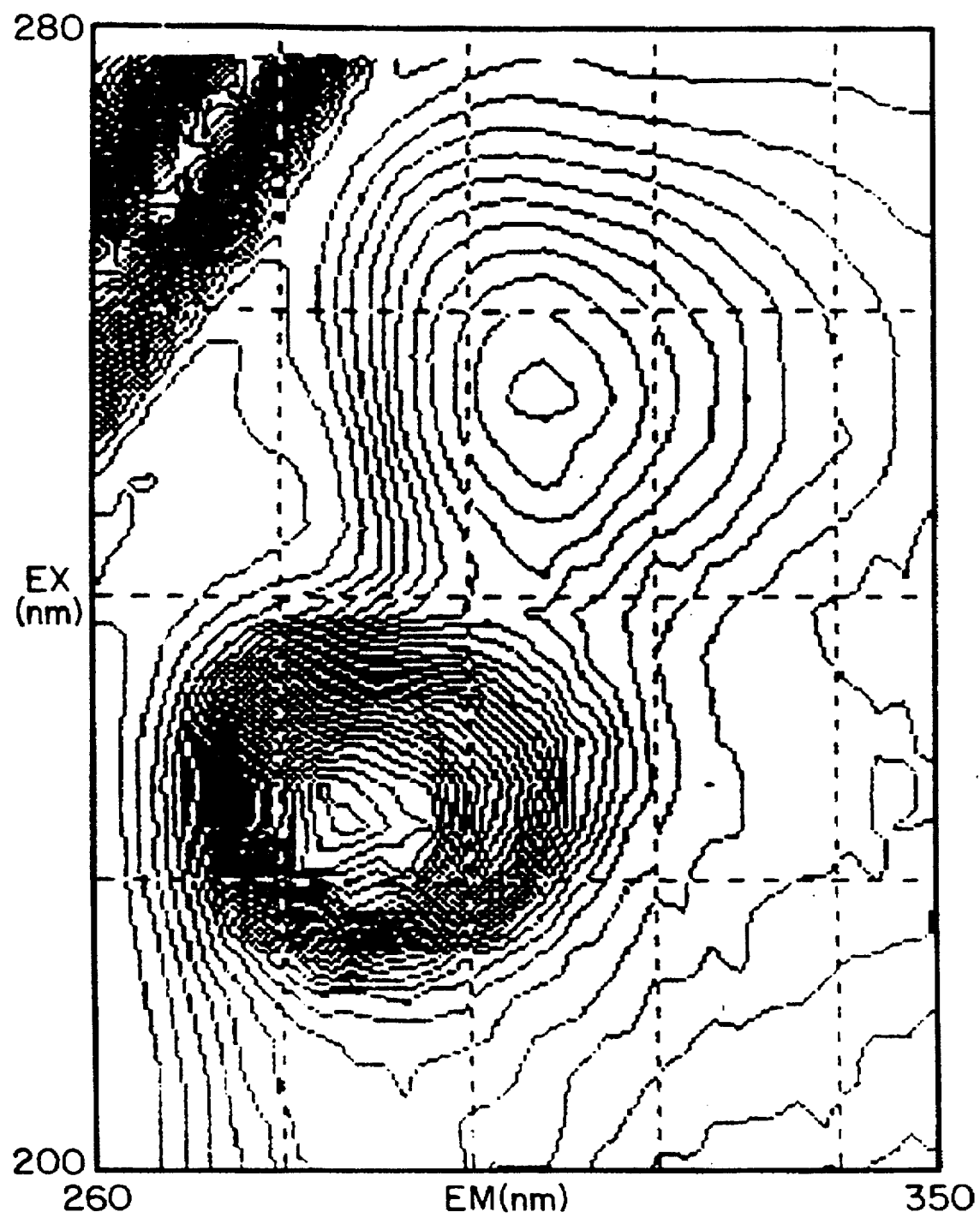
FIG. 5 is a fluorescence contour plot showing the kinetics of the hydrothermal reaction.
Figure 6:
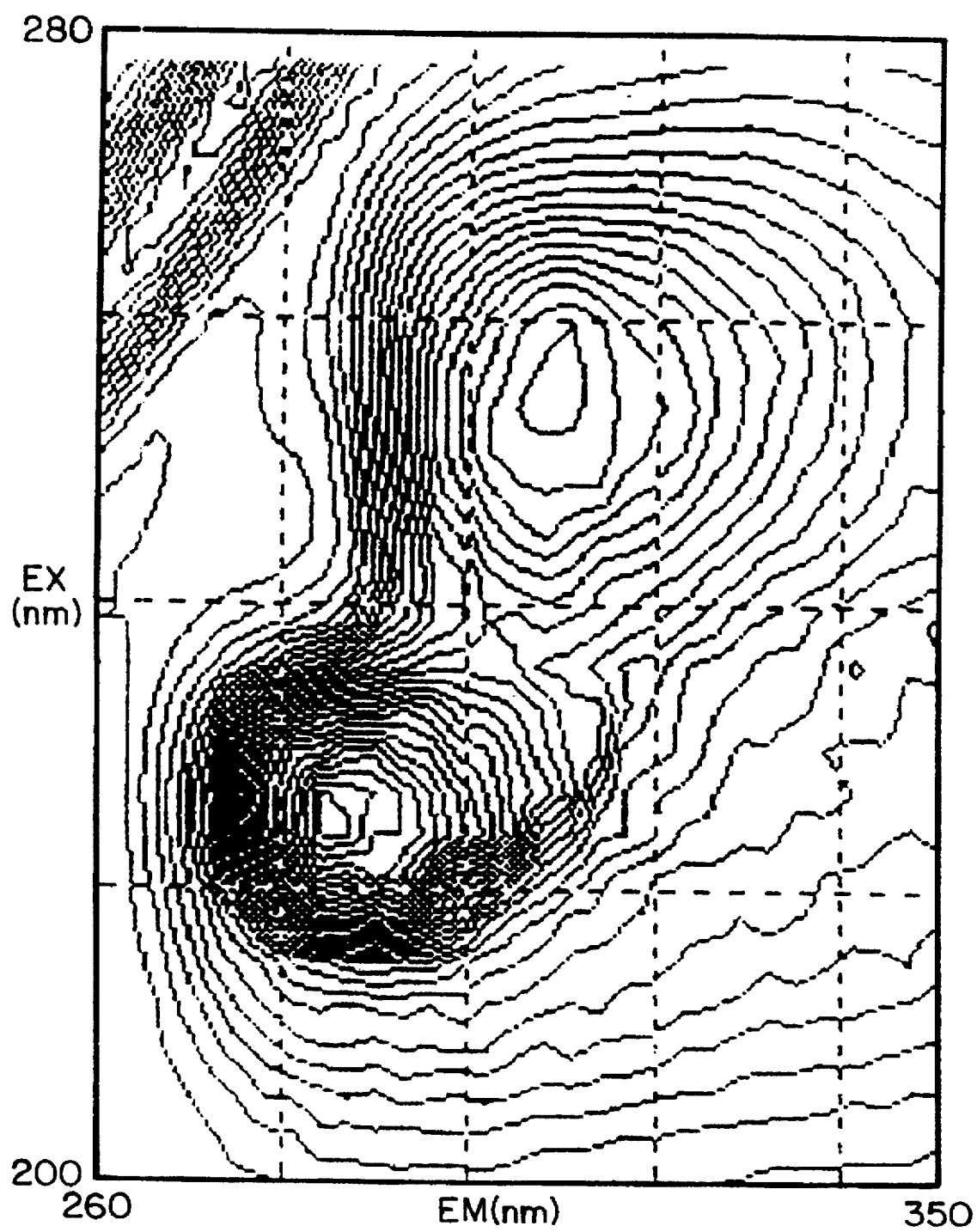
FIG. 6 is a fluorescence contour plot showing the kinetics of the hydrothermal reaction.

The results are summarized in FIGS. 4, 5, and 6. FIG. 4 shows the fluorescence spectrum at the beginning of the test (at approximately 0.1 hours). Since no hydrothermal reaction has yet occurred, the spectrum is simply that of the AA/SS polymer. After heating for seven hours, a new fluorescence feature (spectrophotometrically measured at a different set of wavelengths) has appeared (see FIG. 5), and this is due to a hydrothermal reaction product. Further heating for a total of 29.5 hours caused this reaction product to grow in intensity, with a concomitant decrease in the AA/SS polymer fluorescence, as seen in FIG. 6.

Figure 7:
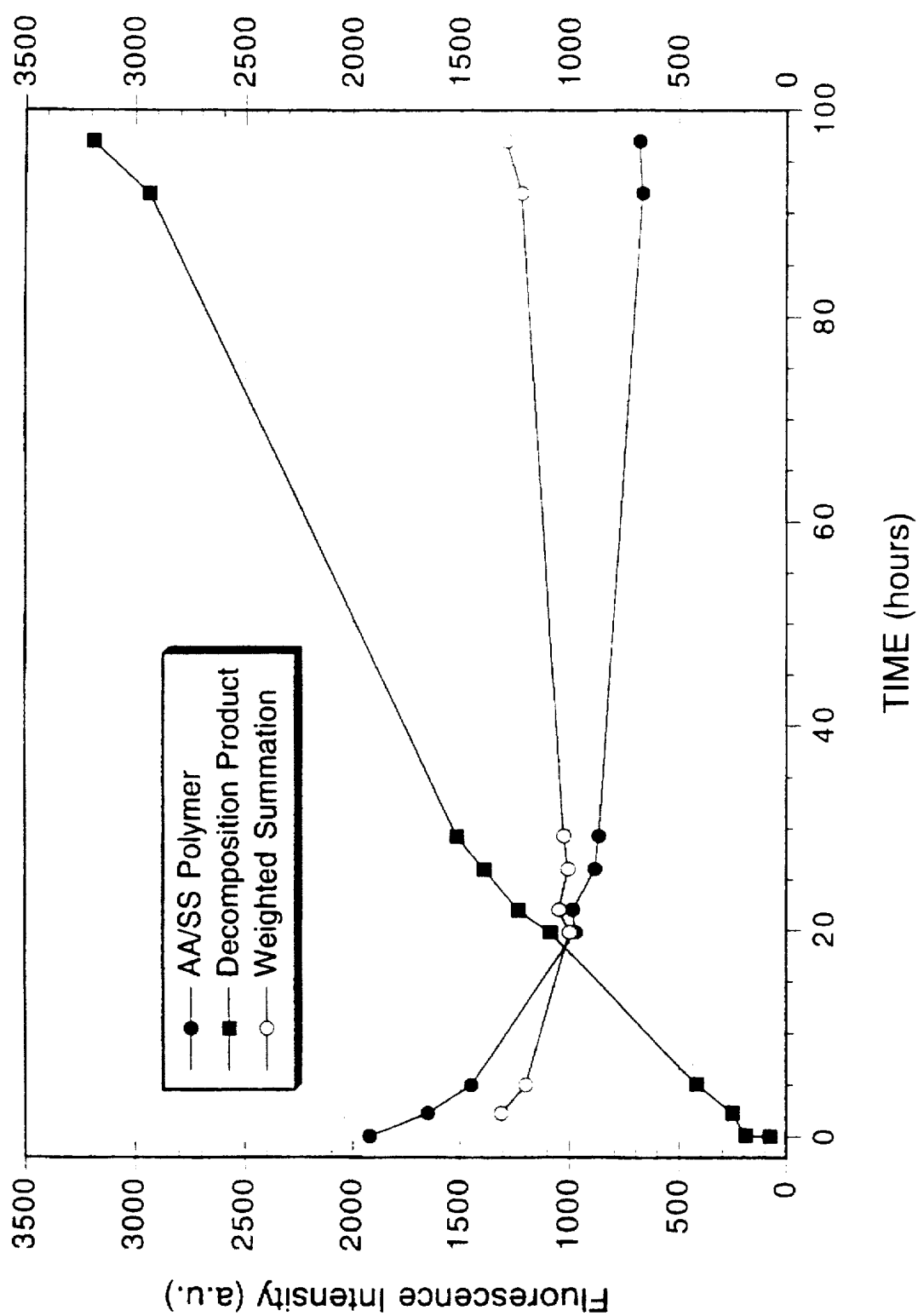
FIG. 7 is a line graph showing that the weighted summation yields a constant.
Figure 8:
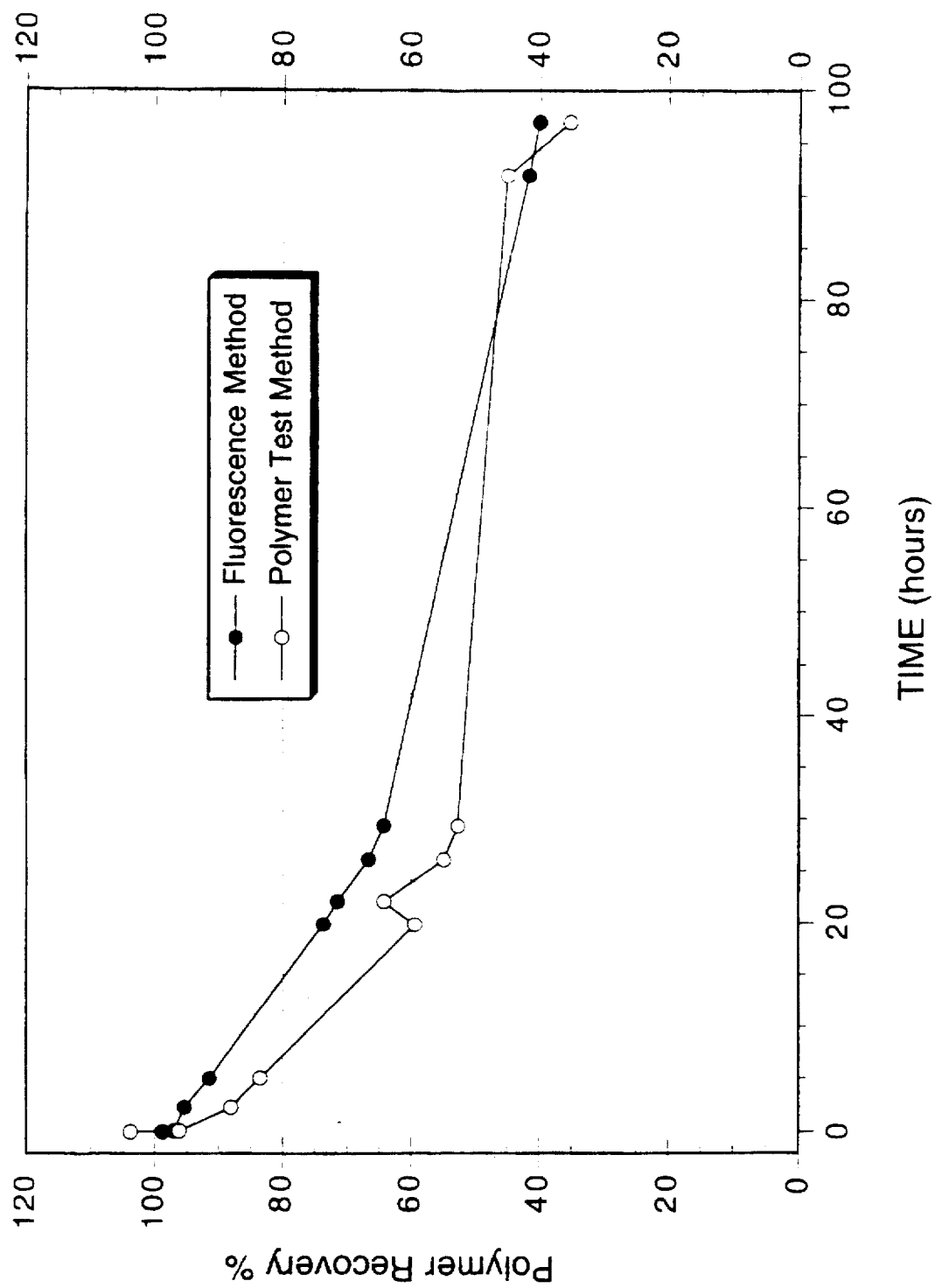
FIG. 8 is a line graph showing fluorescence measurement tracking a polymer recovery test.
Figure 9:
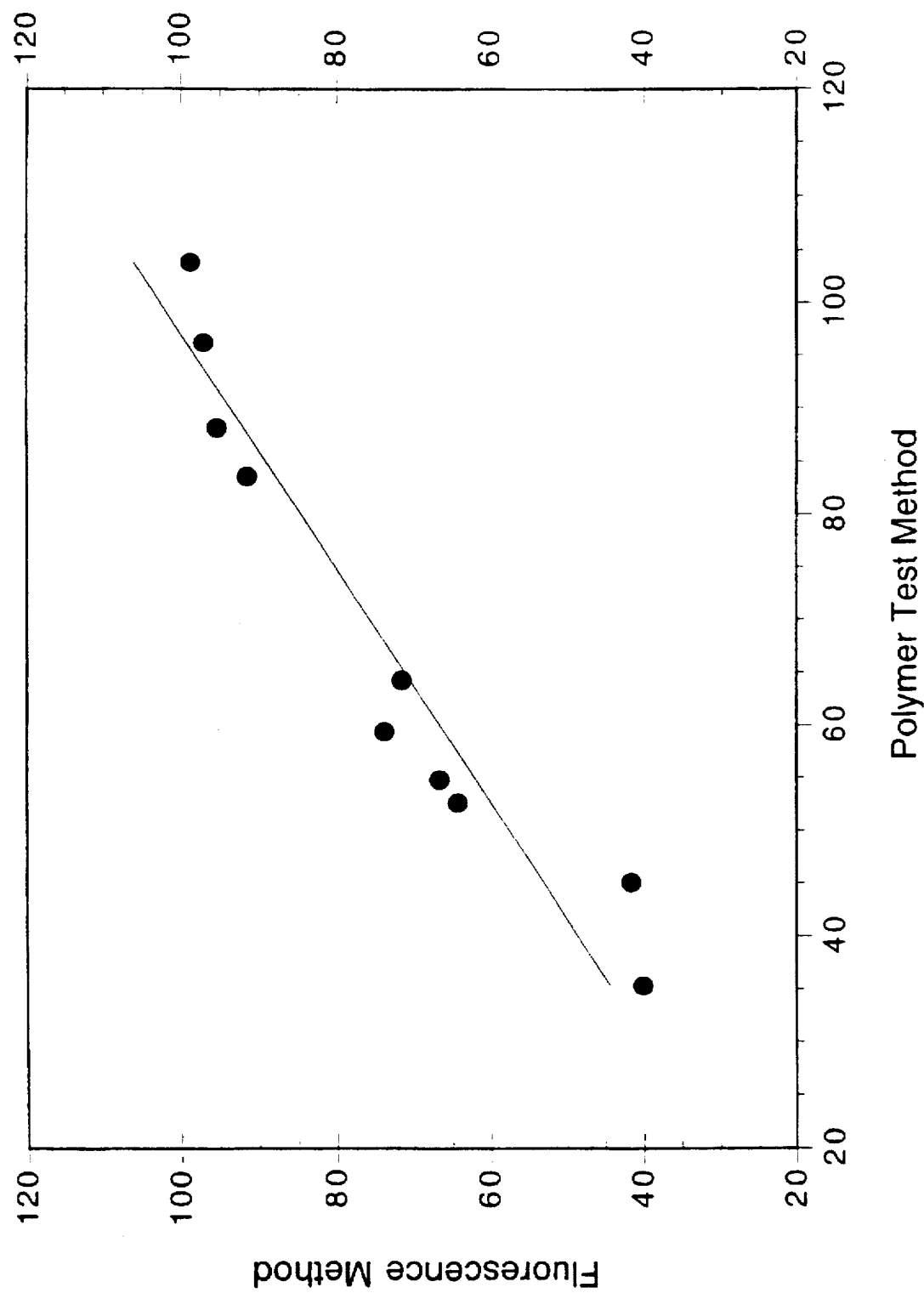
FIG. 9 is a line graph showing the comparision between polymer recovery as measured by a polymer wet chemistry test and by the fluorescence method described in the text.

FIGS. 7, 8, and 9 show a plot of the fluorescence signal of the AA/SS polymer, represented by the dark circles, and the reaction product, represented by the dark squares, as a fiction of time. As the hydrothermal reaction occurs, the polymer fluorescence decreased and the reaction product increased with time. (One would not need to know the chemical identity of the reaction product to exploit this method nor does there need to be only a single reaction product that could be spectrophotometrically measured. A variety of sets of wavelengths could be used to monitor the polymer or the reaction product to follow the progress of the hydrothermal reaction.) A weighted summation of these two signals is very nearly a constant. The weighted summation of the two signals, fluorescence intensity of the AA/SS polymer (90/10) as added to the system, I(poly), and the fluorescence intensity of the reaction product, I(reaction prod), respectively, can be expressed as:

$$I(poly)+k\ I(reaction\ prod)=constant$$

wherein "k" is a weighting constant. Data taken at 600 psig (254° C.); 800 psig (272° C.); and 1000 psig (286° C.) were subjected to a fitting algorithm to extract the best fit value of "k". An example of this fit is shown in FIG. 7.

3) Measurement of Boiler Cycles

Recently, boiler cycles have been measured using an inert tracer, a benchmark method in this area. However, there may be applications wherein it is not desirable to add inert tracers to boiler systems. Even though the AA/SS polymer is not inert, and undergoes the above mentioned partial hydrothermal reaction under boiler conditions, it is still possible to use the AA/SS polymer fluorescence to extract boiler cycles. Empirically, it has been discovered that cycles can be calculated using the following expression:

$$Cycles = f \times \frac{I(poly, bd) + kI(reaction\ prod, bd)}{I(poly, fw)}$$

wherein I(poly, bd) and I(poly, fw) are the fluorescence intensity of the AA/SS polymer in the boiler blowdown and feedwater, respectively. I(reaction prod, bd) is the fluorescence intensity of the hydrothermal reaction product in the blowdown. "k" (weighted summation constant) is the constant extracted from the fitting algorithym described above, and "f" (correction factor) is a correction factor to account for the kinetically rapid initial stage in the hydrothermal reaction of AA/SS polymer.

A demonstration of the determination of cycles of concentration using this method is summarized in Table I. The determination of cycles, using the AA/SS polymer method, were made using values of k and f calculated using data collected from autoclave tests and applied to electric test boiler experiments. Tests were conducted at both 600 and 1000 pounds pressure.

TABLE I

Measurement of cycles of concentration in an electric test boiler operating at 600 psig pressure using a fluorescent inert tracer (fluorescein) and the AA/SS polymer method detailed in this patent application are shown in Table I. Steaming rate of the boiler was held constant at 54 ml/minute, and the blowdown rate was varied.

| Sample | AA/SS Polymer Method Cycles* | Fluorescent Inert Tracer Cycles (Fluorescein)** |
|---|---|---|
| 1 | 12.0 | 11.2 |
| 2 | 11.2 | 10.3 |
| 3 | 10.7 | 9.9 |
| 4 | 30.7 | 28.9 |
| 5 | 30.7 | 29.9 |
| 6 | 26.9 | 26.9 |
| 7 | 26.6 | 24.1 |
| 8 | 28.5 | 27.0 |
| 9 | 34.7 | 29.4 |
| 10 | 47.8 | 47.9 |
| 11 | 10.4 | 10.9 |
| 12 | 9.4 | 10.1 |
| 13 | 10.6 | 10.2 |
| 14 | 26.2 | 24.5 |
| 15 | 27.0 | 25.6 |
| 16 | 25.8 | 24.6 |

*Boiler cycles as measured by the AA/SS polymer fluorescence technique described above.
**Boiler cycles as measured using an inert fluorescent tracer.

TABLE II

Measurement of cycles of concentration in an electric test boiler operating at 1000 psig pressure using a fluorescent inert tracer (fluorescein) and the AA/SS method detailed in this patent application are shown in Table II. Steaming rate of the boiler was held constant at 54 ml/minute, and the blowdown rate was varied.

| Sample | AA/SS Polymer Method Cycles* | Fluorescent Inert Tracer Cycles (Fluorescein)** |
|---|---|---|
| 1 | 8.9 | 10.1 |
| 2 | 9.6 | 9.2 |
| 3 | 16.9 | 19.3 |
| 4 | 15.5 | 16.9 |

*Boiler cycles as measured by the AA/SS polymer fluorescence technique described above.
**Boiler cycles as measured using an inert fluorescent tracer.

4) Polymer Recovery (Thermal-Stress Responsive Polymer)

The hydrothermal reaction of AA/SS polymer under boiler conditions can be monitored spectroscopically, as described above. As a result, it is possible to exploit this reaction to provide a probe of the stress conditions inside a boiler. Thus, fluorescence measurements can be used to determine the fraction of the AA/SS polymer surviving passage through the boiler (referred to as "polymer recovery"). Polymer recovery can be calculated using the expression:

$$\text{Polymer Recovery} = \frac{I(\text{poly}, bd)}{I(\text{poly}, bd) + kI(\text{reaction prod}, bd)} \times 100$$

wherein all of the terms are as described above.

This method is demonstrated in FIGS. 8 and 9. FIG. 8 plots polymer recovery using both the new fluorescence and current wet-chemistry methods. The two methods are in excellent agreement, as demonstrated in FIG. 9, which plots fluorescence polymer recovery versus the current method of polymer recovery. The plot forms a line with a slope nearly equal to 1.0, indicating close correlation.

This fluorescent method of determining polymer recovery has several advantages over the current method. The current method utilizes a wet chemical test requiring two reagents, has moderate precision and accuracy, has a relatively high concentration detection limit, and can be more difficult to perform in the field. This new fluorescent method requires no chemical reagents, has a low concentration detection limit, good precision and accuracy, and is very easy to perform. As an aside, notice that the above equation does not contain any terms that require any measurements from feedwater samples. Thus, it is possible to determine polymer recovery using this method solely from a blowdown sample, and it is not necessary to have knowledge of the boiler operating cycles. The current wet-chemistry method requires measurements to be performed on both blowdown and feedwater samples, and requires an inert tracer to measure boiler cycles.

5) Custom Dosage Optimization

The above described measurement of polymer recovery using fluorescence enables AA/SS polymer to be utilized as a thermal-stress responsive polymer. This thermal-stress responsive polymer can be exploited to accurately determine the optimum product dosage needed for boiler internal treatment. For boilers that expose treatment chemicals to high thermal stress, a high treatment dosage is needed to accommodate the inevitable hydrothermal reaction and destruction of the internal treatment chemical (typically organic molecules). This is recognized in the fact that typically recommended polymer dosage increases with increasing boiler operation pressure. However, operating pressure is only one factor affecting the thermal exposure of an internal treatment product. Additionally, boiler firing rate, holding time, flow dynamics, and riser-tube heat fluxes and other variables all impact the thermal exposure of the treatment. This invention would provide a measurement of the thermal exposure of the treatment and would be sensitive to all of the above factors. Once the thermal exposure of the treatment is known, an accurate determination of the optimal product dosage can be obtained for each boiler system under each specific set of operating conditions. Optimizing dosages in this manner can potentially improve both the performance and the cost-effectiveness of a treatment program.

A specific boiler design can have very different fluid dynamics, based on how each individual boiler is constructed and fired. Additionally, many boilers are designed to allow operation at a wide variety of conditions; and variations of such conditions may alter the optimal dosages of treating agents. One example would be the same boiler design wherein one boiler is fired using natural gas and another boiler is fired by a coal stoker. A second example would be, using the same boiler design, wherein one boiler is fired and another boiler is used as a waste heat boiler. Another example would be, using the same boiler design, wherein one boiler is operated at 600 psig and another boiler is operated at 1000 psig. The fluid dynamics of the boiler system operated at 1000 psig can be dramatically different than the fluid dynamics of the system operated at 600 psig. The dosage of treatment agent must be altered to met the requirements of the boiler system for each set of operating variables.

The following examples are presented to describe preferred embodiments and utilities of the invention and are not meant to limit the invention unless otherwise stated in the claims appended hereto.

Example 1

Aqueous solutions of an 80/20 AA/SS polymer were prepared such that the concentrations of SS moieties was 5×10$^{-5}$M, 2.5×10$^{-5}$M, and 1×10$^{-5}$M, and the resulting solutions passed through an on-line fluorometer. The fluorometer used a mercury lamp for excitation and an photomultiplier tube for fluorescence detection. An optical filter having a transmission maximum at 254 nm with a 10 nm spectral width was used to select the excitation wavelength, and a filter with a transmission centered at 300 nm and a 40 nm spectral width was used to select the detection wavelength. Deionized water was passed through the fluorometer to establish a baseline, and then the five samples were in turn passed through the fluorometer, followed by deionized water to verify the baseline. The resulting fluorescence data as a function of time is shown in FIG. 1. This data demonstrates how fluorescence from AA/SS polymer can be used for on-line feedwater control.

Example 2

Aqueous solutions of a 95/5 AA/SS polymer were prepared such that the concentration of the polymer ranged from 10 to 100 parts per million (ppm), by weight. The resulting solutions were passed through an on-line fluorometer. The fluorometer used a mercury lamp for excitation and an photomultplier tube for detection of the fluorescence. An optical filter having a transmission maximum at 254 nm with a 10 spectral width was used to select the excitation wavelength, and a filter with a transmission centered at 290 nm and a 10 nm spectral width was used to select the detection wavelength. Two calibration solutions, one having 100 ppm polymer and another containing only deionized water, were used to calibrate the instrument to make it possible to convert the fluorescence signal into a measured polymer concentration. A plot of the polymer concentrations measured in this manner versus the known concentrations of the solutions is shown in FIG. 2. The data shows excellent linearity, and can be very accurately fit to a straight line.

Example 3

An electric test boiler at 600 psig pressure was operated at 10 cycles of concentration on feedwater adjusted to pH=10 which contained 10.2 ppm of 99/1 AA/SS polymer having an average molecular weight of 74,000 as measured against polystyrene sulfonate standards, 30 ppm NaCl, and 0.1 ppm of 1,5-naphthalene disulfonic acid (NDSA) as an inert tracer. Over a period of four days, the feedwater concentration of calcium was slowly increased from zero to 5.5 ppm, and the blowdown fluorescence of the inert tracer (NDSA) and the AA/SS polymer were monitored using on-line fluorometers. The NDSA fluorometer used 290 nm for excitation and detected the fluorescence emission at 330 nm, while the AA/SS polymer fluorometer used the same wavelengths as in Example 1. FIG. 3 shows some representative data. At times between zero and two hours, the feedwater Ca (as CaCO$_3$) concentration is 4.5 ppm and the polymer is still remaining soluble in the boiler water. At a time of two hours, the feedwater hardness was suddenly increased to 5.5 ppm, simulating a hardness upset. Shortly afterwards, the AA/SS polymer fluorescence signal in the blowdown began to steadily decrease relative to the NDSA inert tracer, indicating precipitation of the calcium salt of AA/SS polymer. This example shows how this invention can monitor in real time any polymer precipitation due to a sudden hardness upset.

Example 4

An electric test boiler at 600 psig pressure was operated on feedwater adjusted to pH=10 which contained 10.0 ppm of 90/10 AA/SS polymer and 1 ppm fluorescein inert tracer. The steaming rate was set to 54 ml/minute, and the blowdown rate was varied to change the boiler cycles of concentrations. The resulting boiler operating cycles were measured by two independent methods. First, cycles were calculated by dividing the fluorescence intensity of fluorescein in the boiler blowdown by the intensity seen in the feedwater. Second, the cycles were determined by using the method described in this patent, using a value of k=0.319 and f=1.357. The results are summarized in Table I. Excellent agreement is seen between boiler cycles as calculated by these two methods.

Example 5

An electric test boiler at 1000 psig pressure was operated on feedwater adjusted to pH=10 which contained 7.0 ppm of 90/10 AA/SS polymer and 0.5 ppm fluorescein inert tracer. The steaming rate was set to 54 ml/minute, and the blowdown rate was varied to change the boiler cycles of concentrations. The resulting boiler operating cycles were measured by two independent methods. First, cycles were calculated by dividing the fluorescence intensity of fluorescein in the boiler blowdown by the intensity seen in the feedwater. Second, the cycles were determined by using the method described in this patent, using a value of k=0.319 and f=1.357. The results are summarized in Table II. Excellent agreement is seen between boiler cycles as calculated by these two methods.

Example 6

A 10.8 ppm solution of 90/10 AA/SS polymer at pH=11 was heated in an autoclave at 254° C. and 600 psig. After various amounts of time, a sample was collected, and the fluorescence intensity at various excitation and emission wavelengths were obtained. The data are displayed as contour plots in FIG. 4. After 0.1 hours, the characteristic fluorescence spectrum of AA/SS polymer is observed (FIG. 4). After heating for seven hours at 600 psig, a new fluorescence feature is observed to grow in intensity (see FIG. 5). After a period of 29.5 hours, this new band is observed to continue to still further grow in intensity, with a concomitant decrease in the intensity of the AA/SS polymer fluorescent peak, as shown in FIG. 6. This example demonstrates how the hydrothermal reaction of the polymer can be followed using fluorescence methods.

Example 7

A 10.8 ppm solution of 90/10 AA/SS polymer at pH=11 was heated in an autoclave at 254° C. and 600 psig. After various amounts of time, a sample was collected, and the fluorescence intensity at various excitation and emission wavelengths was obtained. As shown in FIG. 7, the fluorescence intensity of the AA/SS polymer (excitation wavelength=228 nm, emission wavelength=275) is observed to decrease in intensity as a function of time as hydrothermal reaction proceeds while the fluorescence intensity of the reaction product (excitation wavelength=290 nm, emission wavelength=370 nm) is observed to increase in intensity as a function of time as the hydrothermal reaction proceeds. A weighted summation of these two quantities, using a weighted summation constant (k) of 0.319, is observed to yield a nearly constant value, as shown in FIG. 7. This fluorescence data was used to calculate the polymer recovery percentage, as described in this patent.

The polymer recovery was also determined by quantifying the amount of surviving polymer using a polymer turbidity test. In this test, a cationic surfactant is used to react with the anionic carboxylate functionality, forming an insoluble polymeric complex. The concentration of this polymeric complex can then be related to the resulting turbidity of the solution. The following equation was applied:

% recovered polymer = 100 ×

$$\frac{\text{(turbidity of polymer in } bd/\text{turbidity of polymer in } fw)}{\text{(Concentration of tracer in } bd/\text{Concentration of tracer in } fw)}$$

Close agreement is seen between the two methods, as shown FIG. 8. This agreement is further highlighted in FIG. 9, which plots the polymer recovery percentage as measured by the fluorescent method described in this patent ("Fluorescence Method") as a function of the polymer recovery percentage as measured by the wet-chemistry polymer turbidity test (Polymer test recovery).

Example 8

An electric test boiler was operated at 10 cycles on feedwater adjusted to pH 10, which contained between 2.0 and 10.0 ppm of 90/10 AA/SS. The boiler operating pressure was varied between 600 and 1500 psig. The polymer recovery was measured using the fluorescence method detailed in the text. The polymer recovery was 98.6%, 92.1%, 71.6% and 40.0% at 600, 1000, 1200, and 1500 psig, respectively.

This is in reasonable agreement with the corresponding values of 96.1%, 85.6%, 76.0%, and 35.3%, respectively, measured with using the traditional wet-chemistry method. This illustrates how polymer recovery can change in a single boiler by varying an operating parameter, in this case pressure. Other parameters, including boiler design, firing, and mass flow rates also influence polymer recovery in any specific industrial boiler. Thus, for a particular boiler, the dosage of polymer fed to the system may be optimized based on the polymer recovery determination.

For example, using the boiler detailed above, and assuming that a concentration of 5.0 ppm of active treatment agent is desired in the boiler and the boiler is operating at 10 cycles, the optimum amount of polymer to be added to the boiler feedwater is 0.51, 0.54, 0.60, and 1.35 ppm for 600, 1000, 1200, and 1500 psig operating pressures, respectively. This concentration will yield a 5.0 ppm concentration of undecomposed polymer in the boiler water trader the cycles and polymer recovery conditions detailed above. The optimum amount of feed will be unique for each individual boiler, and will differ even among boilers operating at the same pressure.

Example 9

Figure 10:
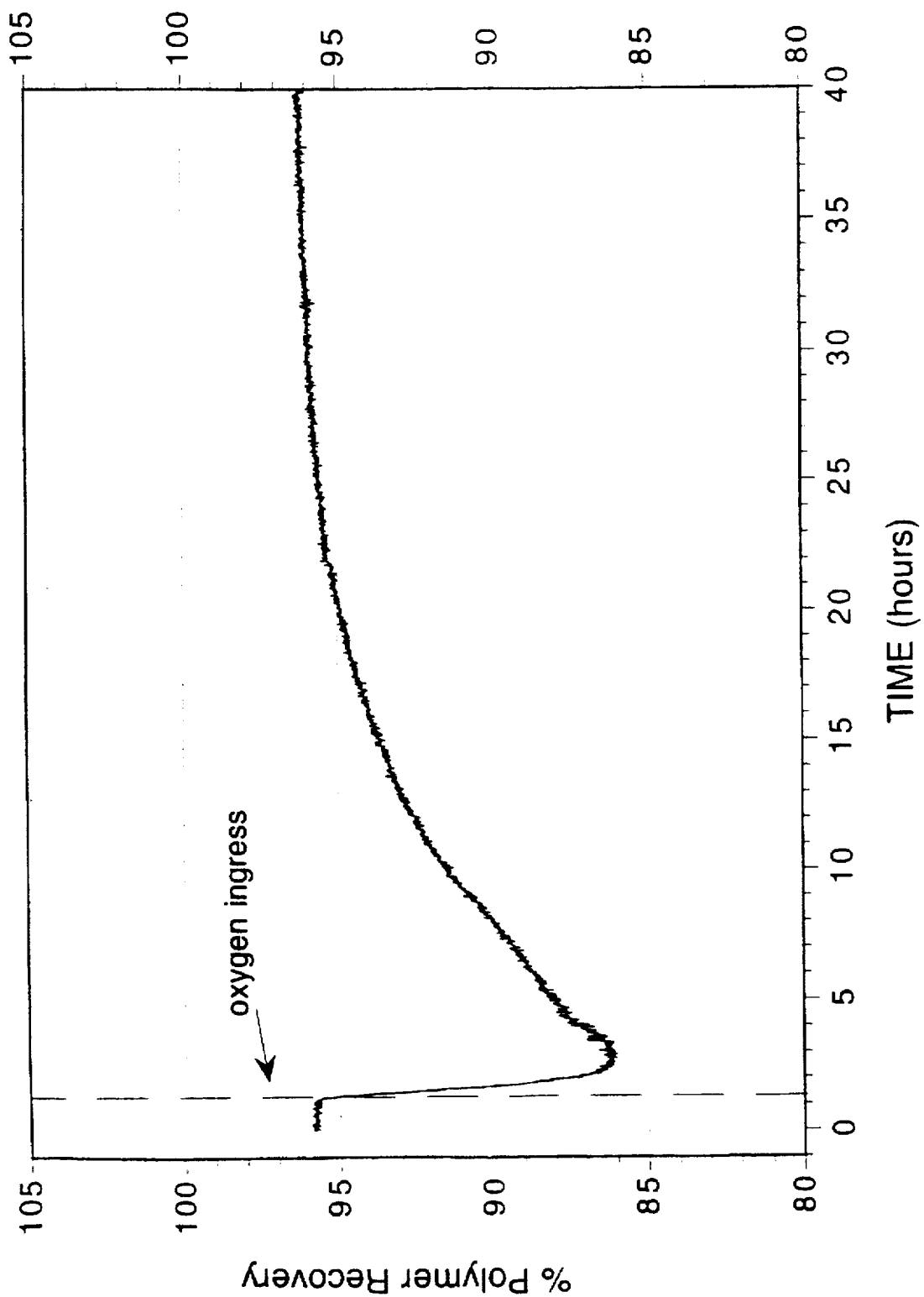
FIG. 10 is a graph showing the decay of the hydrothermal reaction signal following an oxygen upset.

An electric test boiler was operated at 25 cycles on feedwater adjusted to pH 10, which contained 100 ppb of an inert fluorescent tracer, 1.45 ppm of 90/10 AA/SS, and Ca, Mg, and Si at concentrations typical of that found in softened water. The fluorescence intensities of the inert fluorescent tracer (excitation wavelength=470 nm, emission wavelength=520 nm) and the AA/SS hydrothermal reaction product (excitation wavelength=290 nm, emission wavelength=370) were monitored in the boiler blowdown. After a steady state condition was reached, the boiler deaerator was by-passed, and oxygenated feedwater was fed directly into the boiler for about 10 minutes, and then deaeration of the feedwater was resumed. High oxygen concentrations are known to produce rapid reactions with most organic molecules at boiler operating temperatures including Boiler Water Treatment Polymers. The resulting on-line data was used to calculate the polymer recovery (assuming no decomposition of the inert tracer) and the results are shown in FIG. 10. When the oxygenated feedwater was added to the boiler, there was a sharp drop in polymer recovery due to extensive thermal reactions promoted by the oxygen. The polymer recovery gradually rose to the initial value as the reaction products were purged from the boiler via the boiler blowdown. Thus, two identical boilers, having similar operating pressure, firing, and mass flow dynamics, may nonetheless have differing dissolved oxygen concentrations in their feedwater, yielding different polymer recovery values. This difference in polymer recovery would lead to differences in the necessary amount of treatment chemical in the feedwater for optimum performance.

Changes can be made in the composition, operation and arrangement of the method of the present invention described herein without departing from the concept and scope of the invention as defined in the following claims:

We claim:

1. A method of determining boiler cycles of concentration in a boiler water system containing an anionically charged water soluble boiler water treatment polymer, there being a source of a feedwater stream to the system as a first system parameter, a source of a blowdown stream from the system as a second system parameter, as well as a source of the soluble polymer in the boiler water as a third system parameter, and wherein the soluble polymer undergoes a hydrothermal reaction at boiler water system operating conditions, and the soluble polymer contains at least 0.01% mer units of spectrophotometrically emitting moieties bound to the polymer chain, the method comprising the steps of:

a. adding the soluble polymer to a feedwater stream entering the boiler water system;

b. measuring at least one spectrophotometric characteristic of the soluble polymer contained in a sample of the feedwater stream;

c. allowing at least a portion of the soluble polymer to hydrothermally react into a reaction product as the soluble polymer passes through the boiler water system;

d. measuring at least one spectrophotometric characteristic of the remaining soluble polymer and measuring at least one spectrophotometric characteristic of the reaction product contained in a sample of the blowdown stream;

e. converting each of the measured characteristics to electrical signals corresponding the concentration of the soluble polymer in the feedwater stream, the concentration of the remaining soluble polymer in the blowdown stream, and the concentration of the reaction product in the blowdown stream, respectively; and, f. using the concentration of the soluble polymer in the feedwater stream, the concentration of the remaining soluble polymer in the blowdown stream and the concentration of the reaction product in the blowdown stream to determine the boiler cycles of concentration of the boiler system.

2. The method according to claim 1, wherein a sample of the feed water stream containing the soluble polymer is continuously passed through a flow cell and therein continuously measuring at least one spectrophotometric characteristic of the soluble polymer, whereby the boiler cycles of concentration in the system is continuously determined.

3. The method according to claim 1, wherein a sample of the blowdown stream containing the remaining soluble polymer and reaction product is continuously passed through a flow cell and therein continuously measuring at least one spectrophotometric characteristic of the remaining soluble polymer and measuring at least one spectrophotometric characteristic of the reaction product, whereby the boiler cycles of concentration in the system is continuously determined.

4. The method of claim 1 wherein at least one of the spectrophotometrically emitting moieties of said water-soluble polymer is a styrene sulfonate group.

5. The method of claim 1 wherein said water-soluble polymer comprises carboxylate-containing mer units selected from the group consisting of acrylic acid, methacrylic acid, crotonic acid, vinyl acetic acid, 4-methyl-4-pentenoic acid, maleic acid and itaconic acid.

6. The method of claim 5 wherein said water-soluble polymer comprises at least 10% mer units of acrylic acid and water-soluble salts thereof.

7. The method of claim 1 wherein said water-soluble polymer comprises non-carboxylate containing mer units selected from the group consisting of sodium vinylsulfonate, vinyl phosphonic acid, isopropenylphosphate, allyl polyethers, 2-acrylamido-2-methylpropane sulfonic acid, allylsulfonic acid, allyl alcohol, hydroxyethyl methacrylate, N-vinylimidazole, 2-vinyl pyrrolidine, 4-vinyl pyridine and vinyl acetate.

8. The method of claim 1 wherein the spectrophotometric characteristic measured is a fluorescent characteristic.

9. The method of claim 1 wherein said water-soluble polymer is poly(acrylic acid/styrene sulfonate).

10. A method for spectrophotometrically monitoring a soluble polymer recovery value in a boiler water system containing an anionically charged water soluble boiler water treatment polymer, there being a source of a feedwater stream to the system as a first system parameter, a source of a blowdown stream from the system as a second system parameter, as well as a source of the soluble polymer as a third system parameter, and wherein the soluble polymer passes through the boiler water system under boiler water system operating conditions, and the soluble polymer contains at least 0.01% mer units of spectrophotometrically emitting moieties bound to the polymer chain, the method comprising the steps of:

a. adding the soluble polymer to a feedwater stream of the boiler system;

b. allowing at least a portion of the soluble polymer to hydrothermally react into a reaction product as the soluble polymer passes through the boiler water system;

c. measuring at least one spectrophotometric characteristic of the remaining soluble polymer and at least one spectrophotometric characteristic of the reaction product in a sample of the blowdown stream;

d. converting each of the measured characteristics to electrical signals corresponding to the concentration of the remaining soluble polymer in the blowdown stream and the concentration of the reaction product in the blowdown stream, respectively; and, e. using the concentrations of the remaining soluble polymer in blowdown stream and the concentration of the reaction product in the blowdown stream to determine the soluble polymer recovery value within the boiler water system.

11. The method according to claim 10, wherein a sample of the blowdown stream containing the remaining soluble polymer and the reaction product is continuously passed through a flow cell and therein continuously measuring at least one spectrophotometric characteristic of the remaining soluble polymer and at least one spectrophotometric characteristic of the reaction product, whereby the soluble polymer recovery value within the boiler water system is continuously determined.

12. The method according to claim 10, wherein the soluble polymer recovery value for the boiler water system is used to determine an optimum concentration of the soluble polymer needed to effectively treat the boiler water system.

13. The method of claim 10 wherein at least one of the spectrophotometrically emitting moieties of said water-soluble polymer is a styrene sulfonate group.

14. The method of claim 10 wherein said water-soluble polymer comprises carboxylate-containing mer units selected from the group consisting of acrylic acid, methacrylic acid, crotonic acid, vinyl acetic acid, 4-methyl-4-pentenoic acid, maleic acid and itaconic acid.

15. The method of claim 14 wherein said water-soluble polymer comprises at least 10% mer units of acrylic acid and water-soluble salts thereof.

16. The method of claim 10 wherein said water-soluble polymer comprises non-carboxylate containing mer units selected from the group consisting of sodium vinylsulfonate, vinyl phosphonic acid, isopropenylphosphate, allyl polyethers, 2-acrylamido-2-methylpropane sulfonic acid, allylsulfonic acid, allyl alcohol, hydroxyethyl methacrylate, N-vinylimidazole, 2-vinyl pyrrolidine, 4-vinyl pyridine and vinyl acetate.

17. The method of claim 10 wherein the spectrophotometric characteristic measured is a fluorescent characteristic.

18. The method of claim 10 wherein said water-soluble polymer is poly(acrylic acid/styrene sulfonate).

* * * * *